United States Patent [19]
Lahm et al.

[11] Patent Number: 5,534,227
[45] Date of Patent: Jul. 9, 1996

[54] THERMOFORM DISH INSERT

[75] Inventors: William Lahm, Sumter, S.C.; Timothy A. Stevens, Madison, N.J.

[73] Assignee: Becton, Dickinson and Company, Franklin Lakes, N.J.

[21] Appl. No.: 462,932

[22] Filed: Jun. 5, 1995

[51] Int. Cl.⁶ .............................. B01L 3/00; C12M 3/00
[52] U.S. Cl. ................. 422/102; 435/288.4; 435/297.5; 435/305.1; 435/305.2; 435/305.3; 435/305.4; 435/809
[58] Field of Search .......................... 435/288.4, 297.5, 435/305.1, 305.2, 305.3, 305.4, 809; 422/102

[56]       References Cited

U.S. PATENT DOCUMENTS

| | | | |
|---|---|---|---|
| 4,407,943 | 10/1983 | Cole et al. | 435/7 |
| 4,686,190 | 8/1987 | Cramer et al. | 435/291 |
| 4,871,674 | 10/1989 | Matsui et al. | 435/284 |
| 5,026,649 | 6/1991 | Lyman et al. | 435/284 |
| 5,139,951 | 8/1992 | Butz et al. | 435/284 |
| 5,215,920 | 8/1993 | Lyman et al. | 435/284 |
| 5,272,083 | 12/1993 | Butz et al. | 435/240.241 |
| 5,358,871 | 10/1994 | Stevens et al. | 435/284 |
| 5,366,893 | 11/1994 | Stevens et al. | 435/284 |

FOREIGN PATENT DOCUMENTS

0401660A1  12/1990  European Pat. Off. ......... C12M 1/22

*Primary Examiner*—David A. Redding

[57]              ABSTRACT

An assembly and components therefor are disclosed for use in the field of cell and tissue culture. The assembly includes a base having one or more wells, and a cell culture insert which is mountable to the base such that the bottom wall of the insert is suspended within the well. Each well has a generally rectangular configuration such that openings are provided at each corner of the well for introducing fluid to the well. The base includes stepped portions for supporting a pair of flanges extending from diagonally opposite sides of the cell culture insert. A cover is provided for protecting the assembly and maintaining the position of the cell culture insert.

15 Claims, 7 Drawing Sheets

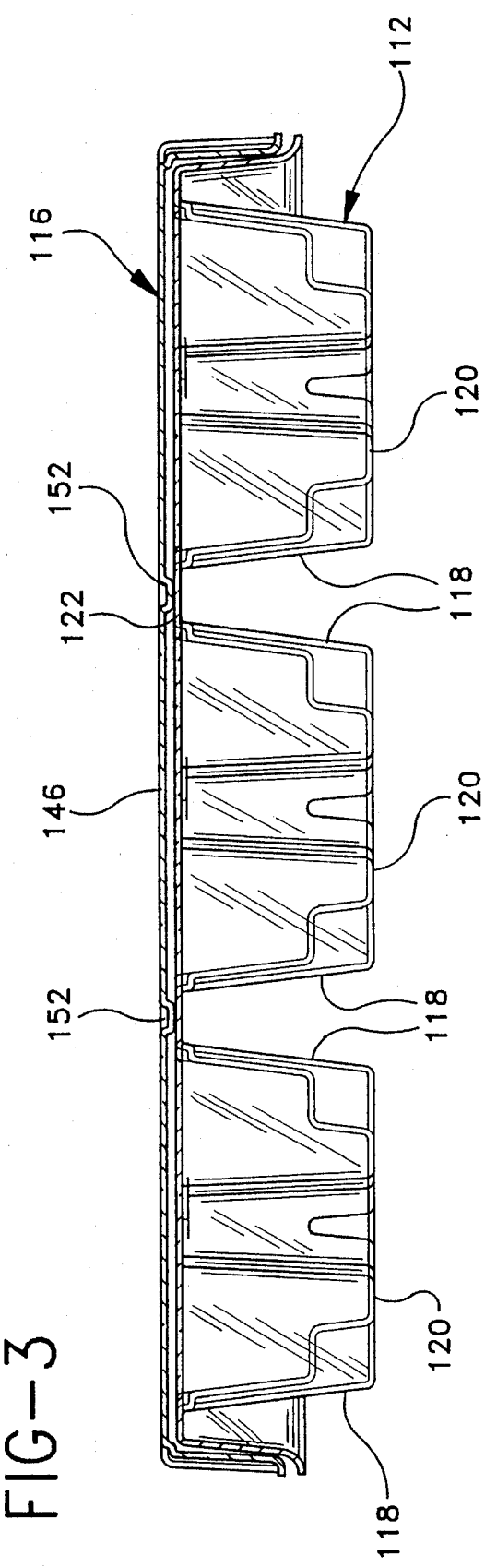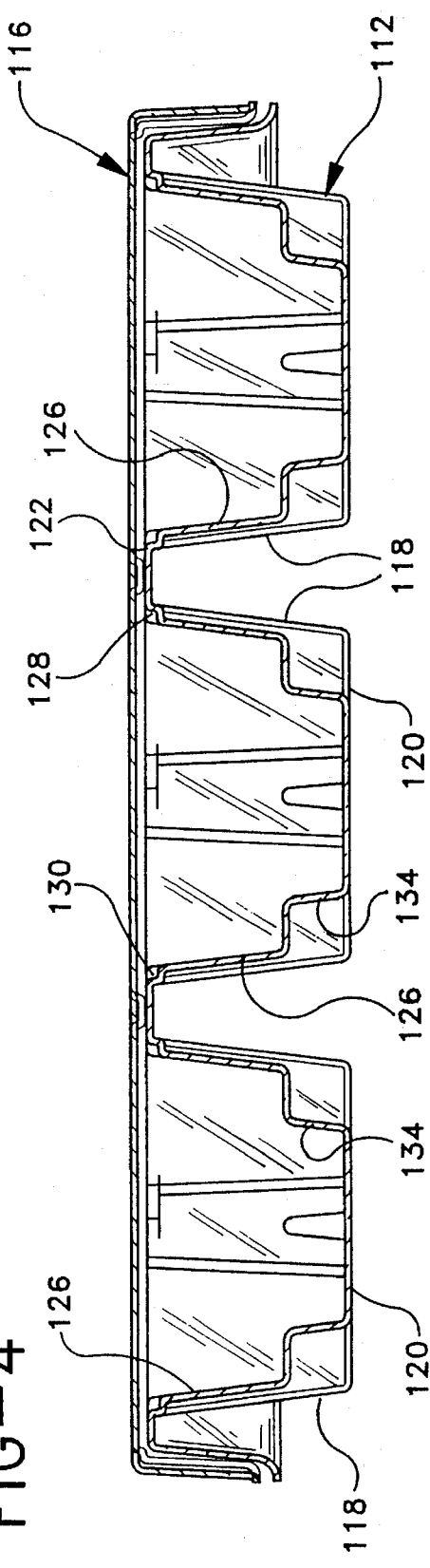

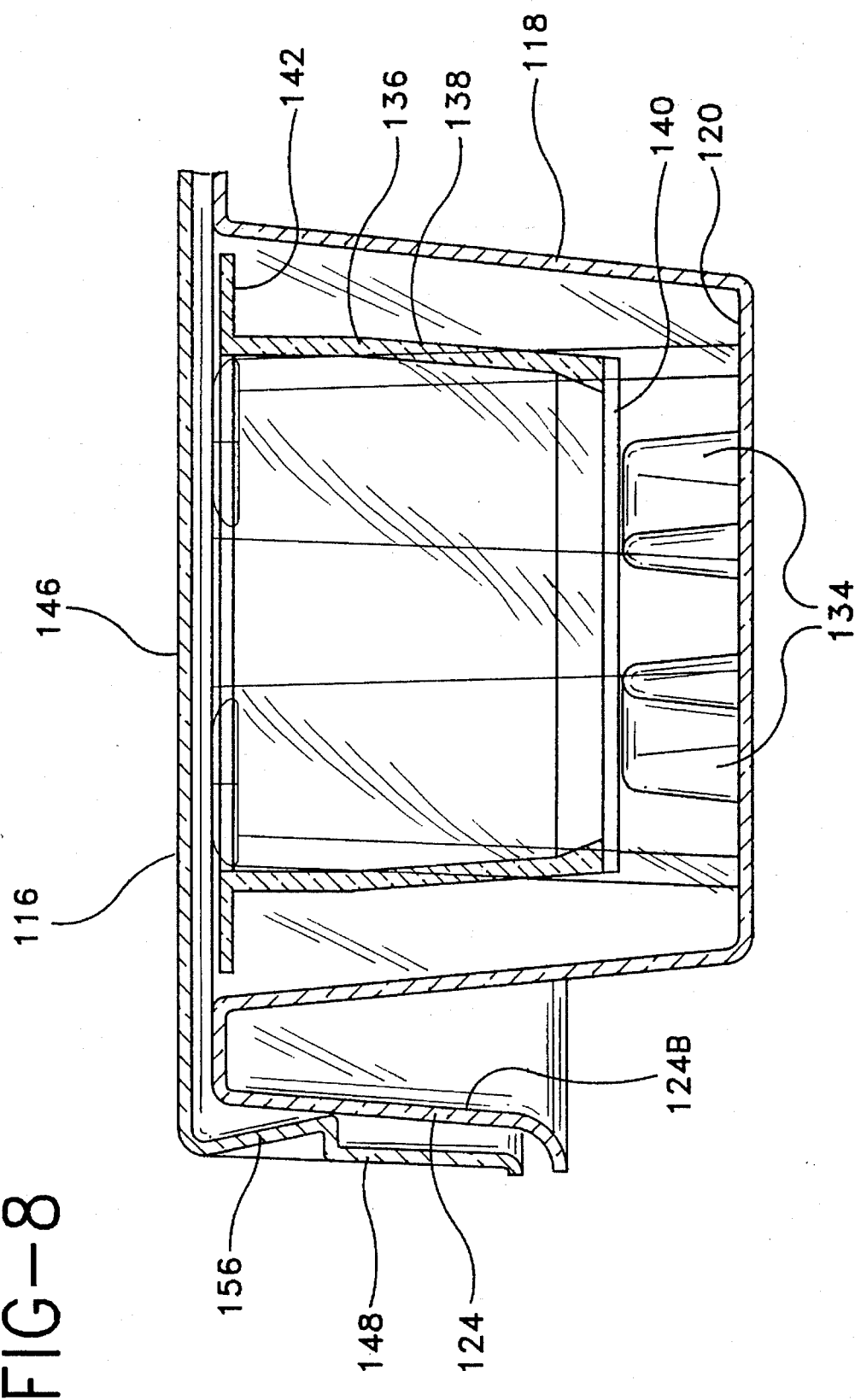

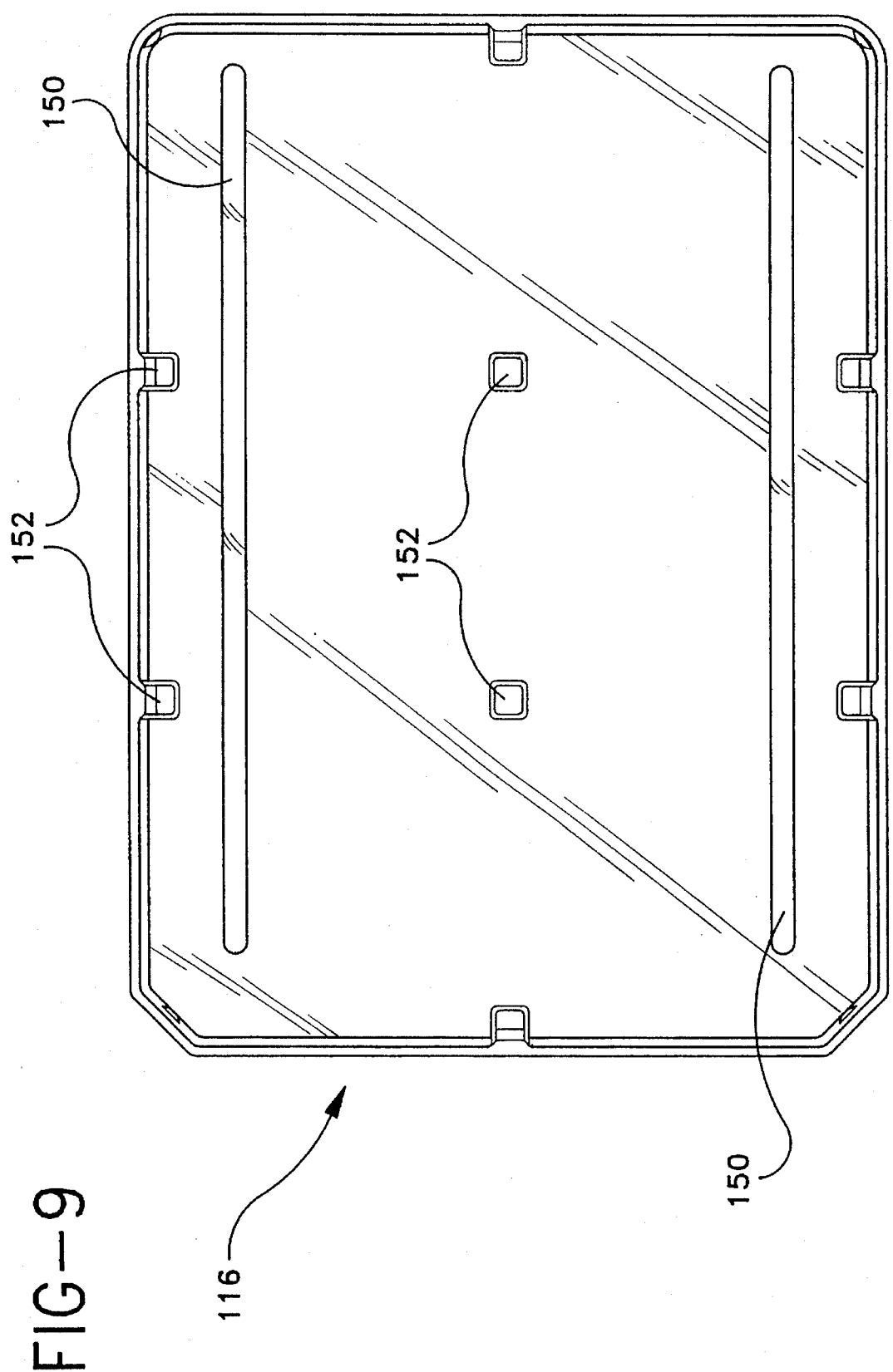

THERMOFORM DISH INSERT

BACKGROUND OF THE INVENTION

1. Field of the Invention

The invention relates to an assembly and an assembly base for growing cells or tissue culture in vitro, and more particularly to a vessel and an assembly wherein cells or other biological materials can be suspended within a nutrient medium.

2. Description of the Related Art

Assemblies of various types have been developed for culturing cells. Such assemblies often include a base defining one or more wells, a cell culture insert removably positioned in a well, and a cover mounted to the base for partially or completely covering the well(s). U.S. Pat. Nos. 4,686,190, 4,871,674, 5,026,649, 5,358,871 and 5,366,893 disclose various assemblies for culturing cells. All of these patented assemblies employ a cell culture insert having a permeable bottom which is suspended within a well by a flange extending peripherally from the top portion of the insert. Other types of inserts include legs which support the insert on the bottom surface of the well such that the permeable bottom of the insert is suspended above the bottom surface.

Most of the prior art assemblies disclosed in the above-referenced patents include generally cylindrical wells and generally cylindrical or frustoconical inserts positioned within the wells. Access to the wells using a pipette or the like may accordingly be relatively difficult. In some of the prior art assemblies, pipette openings are provided in the side walls of the inserts. The size of such openings is limited by the size of the inserts. In other assemblies, limited space is provided between the insert and the side wall of the well. The insert must often be displaced or entirely removed in order to gain access to the well. The space between individual wells of many prior art assemblies is also quite limited.

SUMMARY OF THE INVENTION

It is an object of the invention to provide an assembly to be used for cell or tissue culture. The assembly according to the invention includes a base which defines one or more wells, and a cell culture insert which is removably positioned within at least one of the wells,, Each well includes a generally rectangular upper opening having a plurality of corner portions. Access to the well is provided through one or more of the corner portions of the well opening when the cell culture insert is positioned within the well.

In accordance with a preferred embodiment of the invention, the well includes two pairs of opposing, generally parallel walls defining four corner portions. The cell culture insert is positioned within the well such that an opening is defined between the top portion of the insert and at least one of the corner portions. The opening provides access to the bottom of the well. Access openings are preferably provided at all four corner portions of the well.

The walls of each well include stepped portions for supporting a pair of opposing flanges of a cell insert. The stepped portions prevent rotation of the insert with respect to the well. The insert preferably includes a pair of flanges which extend in opposite directions from the body of the insert. The flanges are positioned upon the stepped portions of the side walls of the well.

A base for supporting a cell culture insert is also provided by the invention. The base includes one or more wells, each well including two pairs of opposing side walls and a bottom wall. Protrusions extend inwardly from the side walls. Each protrusion includes a step for supporting the rim of a cell culture insert. Each step includes a vertical surface extending at an oblique angle with respect to the adjoining side wall. This allows the insert to be mounted diagonally with respect to the well. An elongate ridge preferably extends from each protrusion towards the center of the well. The ridges are substantially shorter in height than the side walls.

DESCRIPTION OF THE DRAWINGS

FIG. 3 is a sectional view taken along line 3—3 of FIG. 1;

FIG. 4 is a sectional view taken along line 4—4 of FIG. 1;

FIG. 8 is an enlarged sectional view taken along line 8—8 of FIG. 1, and

FIG. 9 is a top plan view of the cover for the assembly.

DETAILED DESCRIPTION OF THE INVENTION

Figure 1:
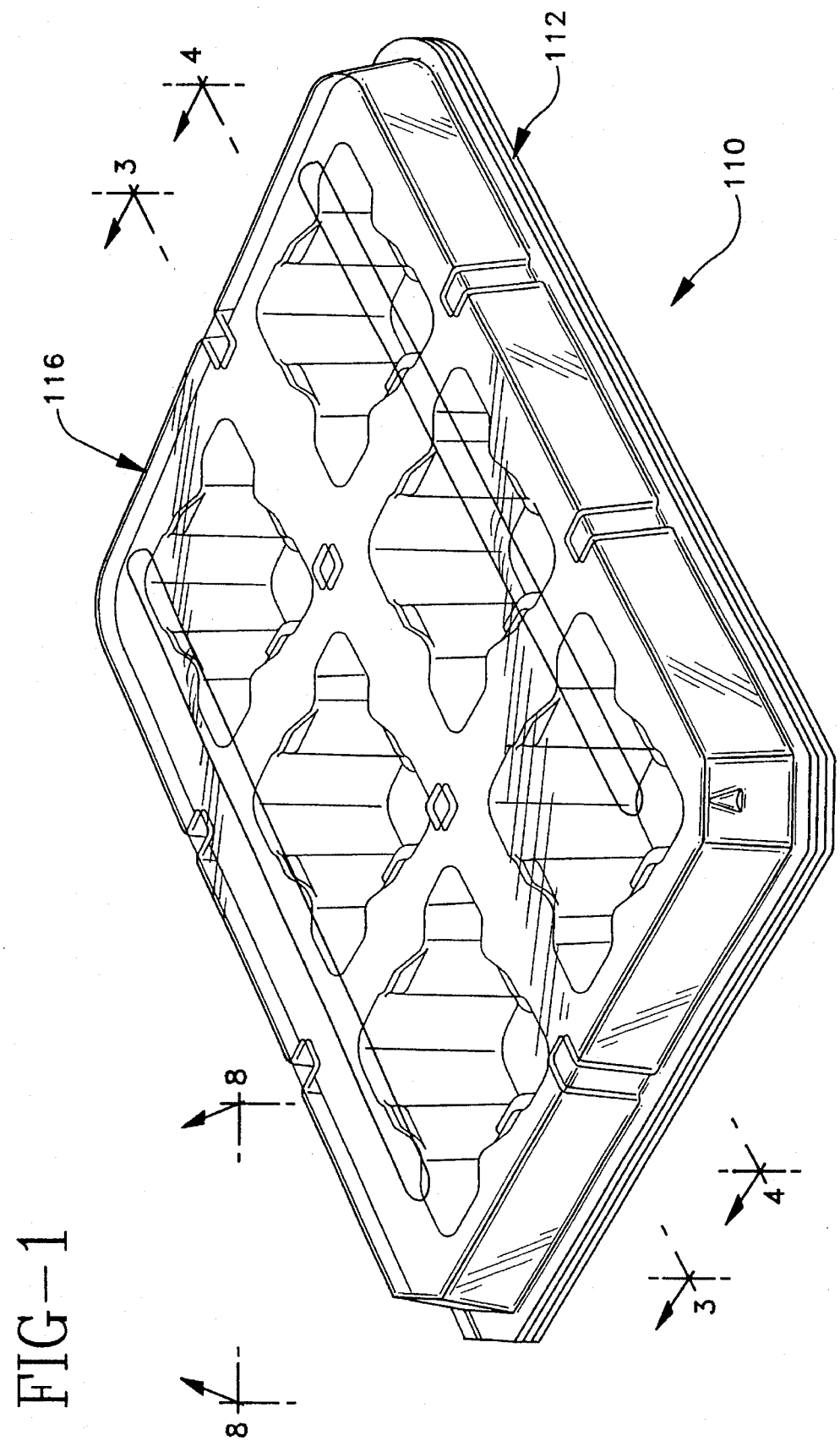
FIG. 1 is a top perspective view of a cell culture assembly according to the invention.

A preferred embodiment of the invention is shown in FIGS. 1–8. An assembly is provided which includes a transparent base 112 including six wells, and one or more cell culture inserts 114 which can be removably mounted to the base. A cover 116 is designed to fit over the base and insert(s).

The base 112 of the assembly includes a plurality of substantially vertical walls 118 and substantially horizontal bottom walls 120. These walls define a multi-well structure, with each well opening having a generally square configuration. Each well is separated from adjoining wells by a horizontal wall portion 122. A peripheral flange 124 extends from the horizontal wall portions. The flange 124 includes a horizontal portion 124A which is coplanar with the wall portions 122 separating the individual wells, a vertical portion 124B, and an outwardly extending lip 124C. Each wall portion is preferably at least about ten millimeters in width.

Figure 7:
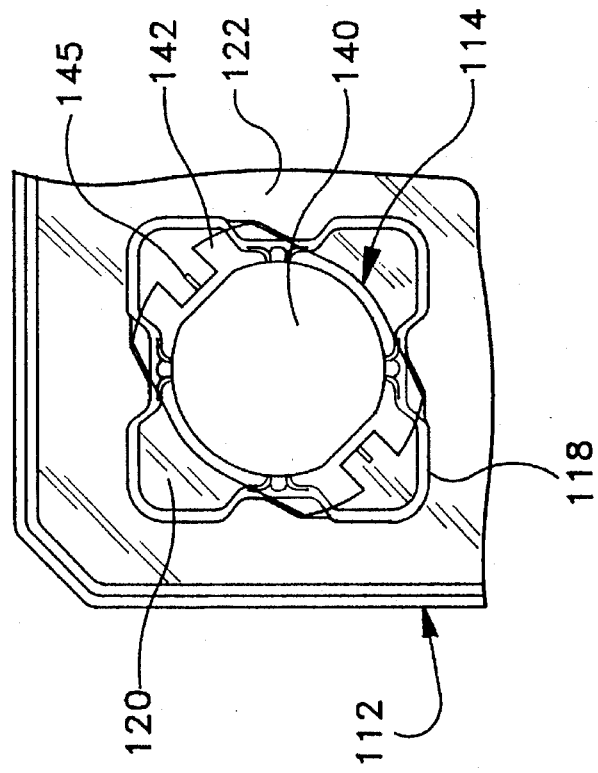
FIG. 7 is a top plan view of a corner portion of the base showing a cell culture insert positioned within a well.

Each vertical wall 118 includes an inwardly extending protrusion 126 in the form of a column. Each protrusion is located at substantially the midpoint of each vertical wall bounding each well. The protrusions are accordingly formed as opposing pairs. Each protrusion includes a flat surface 126A which is parallel to the flat surface of the opposing protrusion. The protrusions are generally trapezoidal in cross section. FIG. 7 most clearly shows these features. Corresponding trapezoidal depressions are formed in the outer surfaces of each well.

Figure 5:
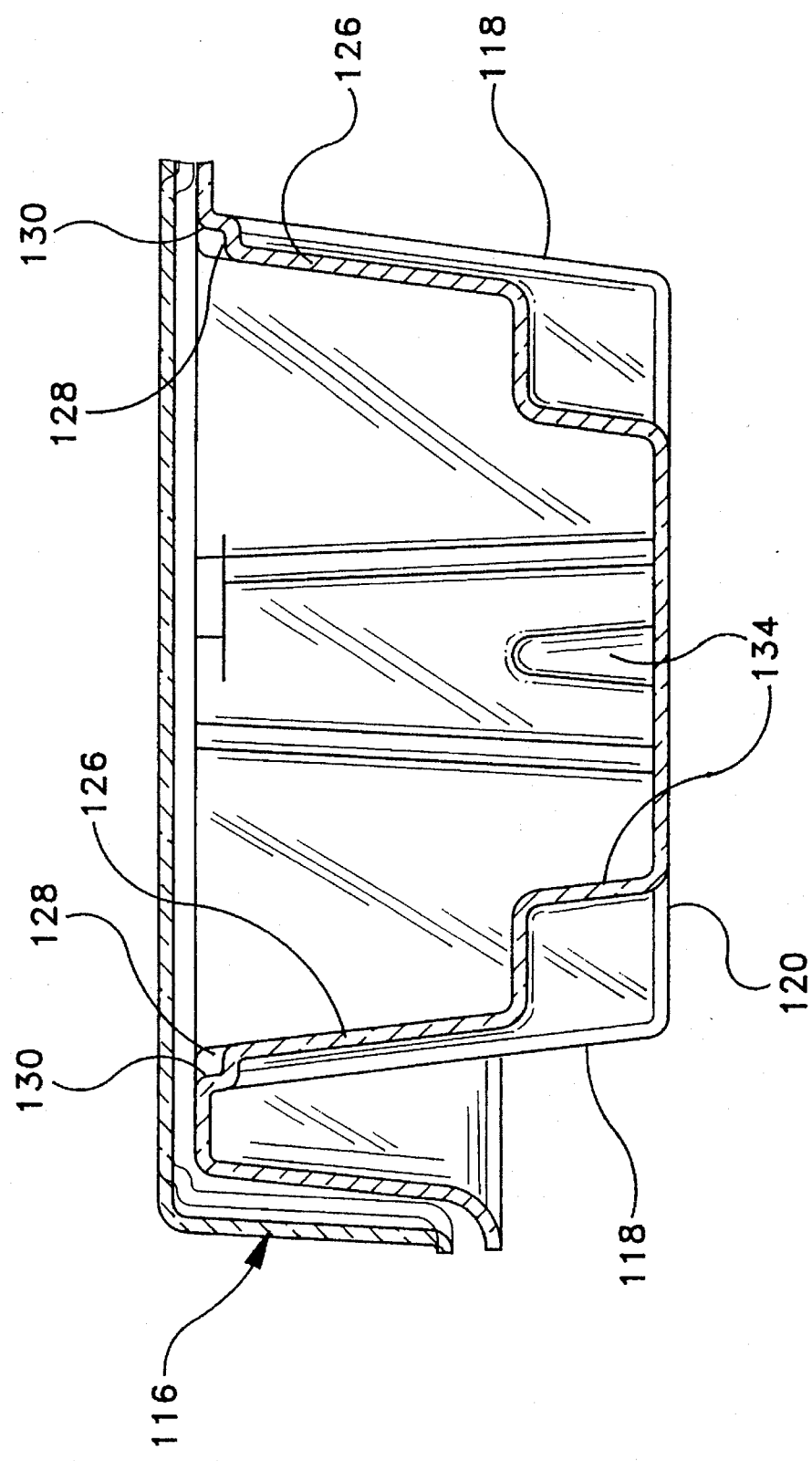
FIG. 5 is an enlarged sectional view of an end portion of the base and cover of the assembly.
Figure 6:
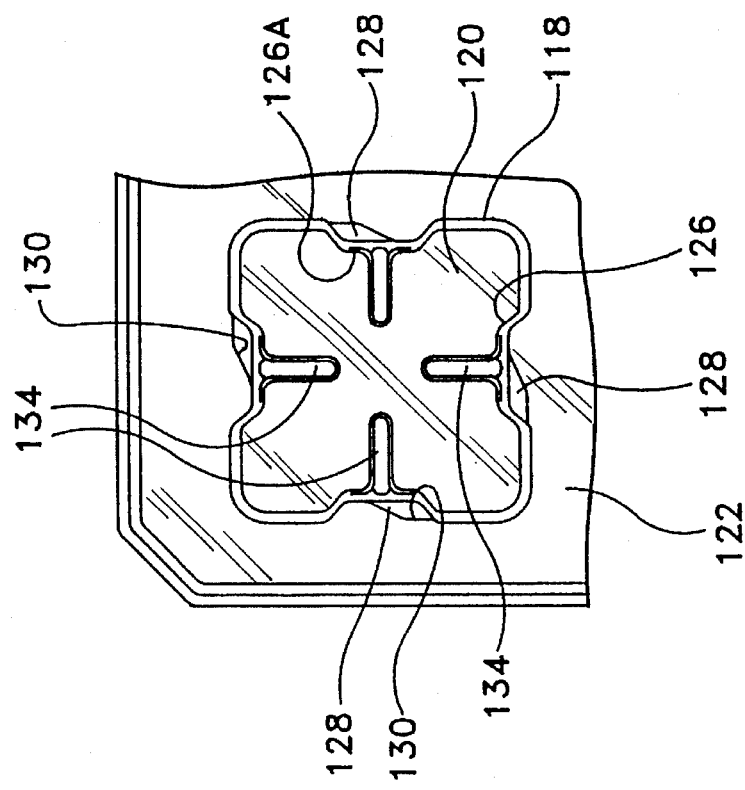
FIG. 6 is a top plan view of a corner portion of the base of the assembly.

A step including a horizontal surface 128 and a vertical surface 130 is formed at the top of each protrusion, as shown in FIG. 5. The vertical surfaces 130 include portions which extend at oblique angles with respect to the vertical walls 118 which they respectively adjoin, as best shown in FIG. 6.

A plurality of discrete, ridge-like projections 134 extend upwardly from the bottom wall 120 of each well. The projections extend substantially perpendicularly with respect to the respective protrusions 126 which they adjoin. The projections 134 are equal in height, and are substantially shorter than the height of the side walls 118. They extend towards the center of the well.

The cell culture insert 114 may be substantially the same as that disclosed in U.S. Pat. Nos. 5,358,871 and 5,366,893. Each insert includes a transparent body 136 comprising a generally cylindrical or frustoconical wall 138. A microporous membrane 140 is affixed to the bottom edge of the wall 138. A pair of flanges 142 extend outwardly from diametrically opposing portions of the top edge of the body. The flanges 142, which may also be referred to as rims, rest upon the horizontal surfaces 128 of the respective steps when the insert is mounted to the base. Portions of the edges of the flanges adjoin the vertical surfaces 130 of the steps, thereby preventing significant horizontal displacement or rotation of the insert. Each flange includes a centrally located notch which facilitates its use in the culture vessel shown in U.S. Pat. No. 5,358,871. The body of the insert further includes a pair of outwardly projecting tabs 145 which provide stability if the insert is used in a cylindrical well. Both the notch and the tabs can be omitted if the insert 114 is only to be used in a base having square wells, as disclosed herein. These features simply provide flexibility for use in a number of different bases.

Figure 2:
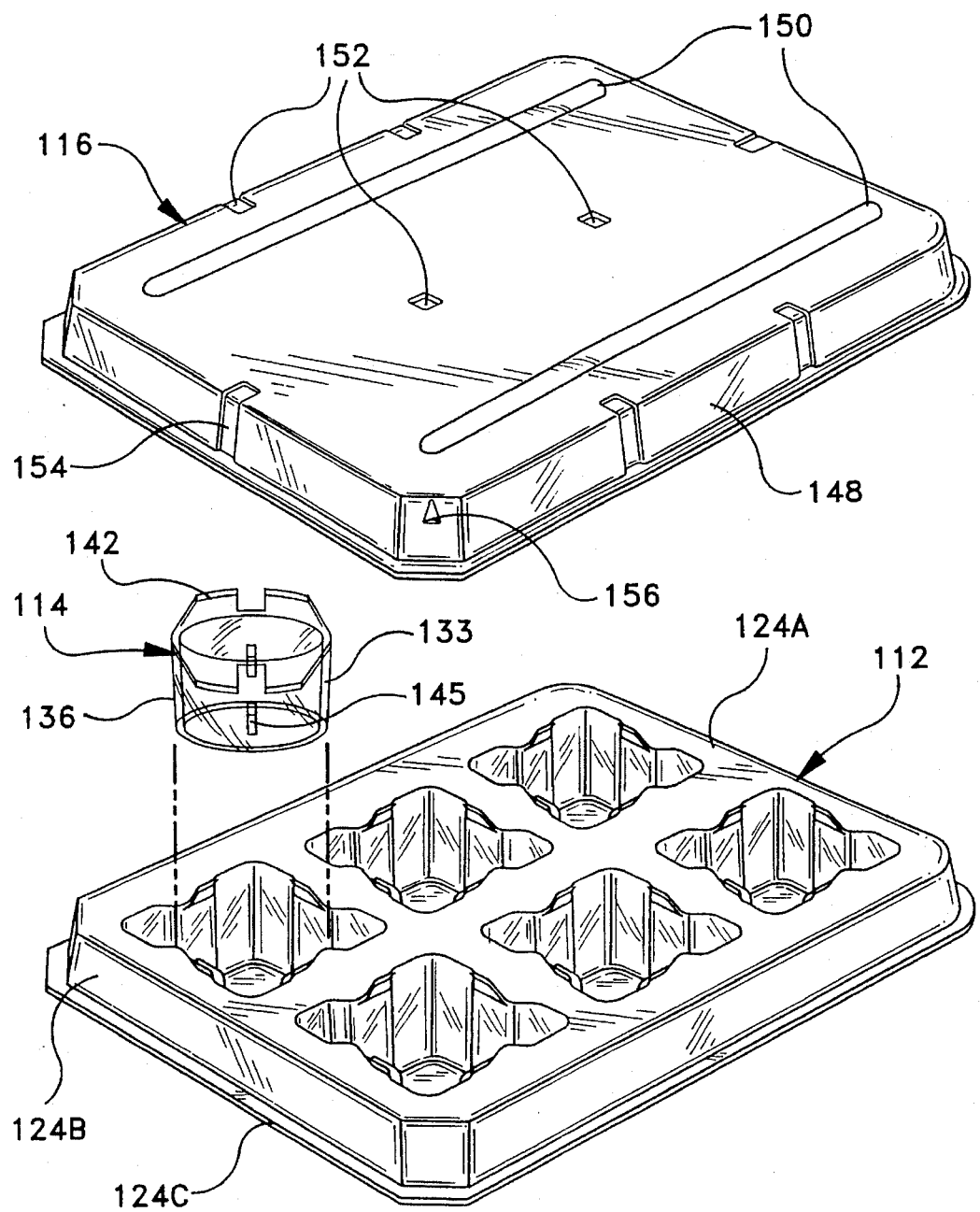
FIG. 2 is an exploded, top perspective view thereof.

The cover 116 includes a top wall 146 and a downwardly extending flange 148. Like the base, it is preferably made from a clear, semi-rigid, plastic material such as polystyrene or PETG. The top wall of the cover includes a pair of parallel ridges 150 which facilitate stacking of the covered assembly. It further includes downwardly extending depressions 152 which engage the upper surface of the base as shown in FIGS. 3 and 4. The flange 148 of the cover includes inwardly extending depressions 154 adjoining the depressions 152 on the edge portions of the cover, as best shown in FIG. 2. The inwardly extending depressions 154 are engageable with the vertical portion 124B of the flange of the base 112. Finally, triangular indentations 156 are formed in the corner portions of the cover flange 148. As shown in FIG. 8, these indentations engage the corner portions of the flange 124. The depressions 152, 154 and indentations 156 prevent the cover 116 from sticking to the base 112.

In use, one or more cell culture inserts 114 are positioned within the wells of the base 112. The wells are preferably numbered for easy reference. Numerals can be provided in one of the corner portions of each bottom wall 120 so that they are visible even with the inserts in place.

The steps defined by the wall protrusions 126 are constructed such that the radially extending flanges 142 of each insert are positioned near diagonally opposing corner portions of each well. This provides two relatively large openings between the upper rim of the insert and two diagonally opposing corner portions of the well, and two smaller openings between the outer edge of each flange and the other diagonally opposing corner portions of the well. All of the openings are preferably sufficiently large to allow the insertion of a pipette therein, though it will be easier to employ the larger openings for this purpose.

The steps are designed to receive the flanges 142 of the inserts and to maintain the inserts in substantially fixed positions relative to the wells. While some freedom of movement is allowed in the horizontal plane, the vertical surfaces 130 of the steps prevent significant translational or rotational movement of the inserts.

The height of the insert body is such that the microporous membrane 140 is positioned just above (e.g. 1–3 millimeters) the top surfaces of the ridge-like projections 134, and well above the bottom wall 120 of the well. In a preferred embodiment of the invention, the ridge-like projections are about eight millimeters in height. The inserts may be between about fifteen and twenty millimeters in height. The insert body diameter in a preferred embodiment of the invention is about thirty millimeters. A distance of about ten millimeters between the rim of the insert body and each of two corner portions of the well provides more than ample space to insert a pipette or other instrument into the well without displacing the insert.

Once a medium has been deposited in one or more wells, and tissues or cells have been deposited on the membrane 140, the tissue or cell culture can be nourished by the medium. The cover 116 is applied to the base to prevent contamination of the assembly. As all components of the assembly are substantially transparent, experiments conducted in the assembly can be observed without removing the cover. As discussed above, the various depressions 152, 154 and indentations 156 in the cover insure a relatively loose fit over the base. This allows the cover to be removed easily without disturbing the base or wells.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An assembly for growing cells or tissue cultures, comprising:

a base defining a well bounded by a bottom wall and a plurality of side walls, said side walls defining a generally rectangular well opening including a plurality of corner portions;

a plurality of support surfaces defined by said base, and a cell culture insert removably mounted to said base, said cell culture insert including a body defining an enclosure, a top end and a bottom end, a permeable membrane secured to said bottom end of said body, and a pair of flanges extending radially outwardly from diametrically opposing portions of said body;

said flanges being supported by said support surfaces and extending towards diagonally opposed corner portions of said well opening, whereby a pair of relatively large openings are defined between said body and a pair of diagonally opposed corner portions of said well opening, a pair of relatively smaller openings are defined between said flanges and a second pair of diagonally opposed corner portions of said well opening, and said permeable membrane is suspended within said well above said bottom wall of said well.

2. An assembly as described in claim 1, wherein said base defines a plurality of wells, each of said wells including a generally rectangular well opening.

3. An assembly as described in claim 1, wherein said well is bounded by two pairs of opposing, generally parallel side walls and said bottom wall, each of said side walls including a protruding portion extending into said well, each of said protruding portions including a step having a vertical surface and a horizontal surface, said flanges of said insert being supported by said horizontal surfaces.

4. An assembly as described in claim 3, wherein each of said vertical surfaces of said steps includes a portion extending obliquely with respect to an adjoining portion of one of said side walls.

5. An assembly as described in claim 3, wherein said vertical surfaces of said steps adjoin said flanges and limit the translational and rotational movability of said insert with respect to said well.

6. An assembly as described in claim 1 including a plurality of ridge-like projections extending upwardly from said bottom wall, each of said ridge-like projections adjoining one of said side walls, said ridge-like projections being substantially shorter in height than said side walls.

7. An assembly as described in claim 2, wherein said base includes a peripheral flange including a horizontal portion and a generally vertical portion, said generally vertical portion being in opposing relation to a plurality of said wells.

8. An assembly as described in claim 7 including a cover mounted to said base, said cover including a top wall and a flange extending downwardly from said top wall, said top wall including a plurality of depressions engaging said base, and said flange of said cover including inwardly extending depressions engaging said generally vertical portion of said flange of said base.

9. An assembly as described in claim 8, wherein said top wall of said cover is substantially rectangular, said top wall including a pair of elongate, parallel ridges extending thereacross.

10. A base for receiving a plurality of cell culture inserts, comprising:

a plurality of wells, each well including a bottom wall and a pair of opposing side walls, each of said wells including a generally rectangular well opening;

each of said side walls of said respective wells including a step defined therein, each of said steps including a substantially horizontal surface and a substantially vertical surface, said vertical surface of each step including a portion extending obliquely with respect to one of said side walls, whereby a cell culture insert having a pair of diametrically opposing flanges can be positioned within said wells such that said flanges are supported by said horizontal surfaces and are positioned near diagonally opposing corner portions of said well opening.

11. A base as described in claim 10, wherein each of said side walls includes a protruding portion extending into said well, said respective steps being defined by said respective protruding portions.

12. A base as described in claim 10 including a plurality of ridge-like projections extending inwardly from each said bottom walls, each of said ridge-like projections adjoining one of said side walls, said ridge-like projections being substantially shorter in height than said side walls.

13. A base as described in claim 10, wherein said base includes a peripheral flange including a horizontal portion and a generally vertical portion, said generally vertical portion being in opposing relation to a plurality of said wells.

14. A base assembly as described in claim 13 including a cover mounted to said base, said cover including a top wall and a flange extending downwardly from said top wall, said top wall including a plurality of depressions engaging said base, and said flange of said cover including inwardly extending depressions engaging said generally vertical portion of said flange of said flange.

15. A base as described in claim 10, wherein each of said wells is separated by a wall portion having a width of at least about ten millimeters.

* * * * *